(12) United States Patent
Müller

(10) Patent No.: US 6,271,413 B1
(45) Date of Patent: Aug. 7, 2001

(54) PROCESS FOR PRODUCING POLYTETRAMETHYLENE ETHER GLYCOL DIESTER ON ALUMINIUM MAGNESIUM SILICATE CATALYSIS

(75) Inventor: Herbert Müller, Frankenthal (DE)

(73) Assignee: Korea PTG Co., Ltd., Ulsan (KR)

( * ) Notice: Subject to any disclaimer, the term of this patent is extended or adjusted under 35 U.S.C. 154(b) by 0 days.

(21) Appl. No.: 08/913,553

(22) PCT Filed: Mar. 14, 1996

(86) PCT No.: PCT/DE96/00452

§ 371 Date: Oct. 3, 1997

§ 102(e) Date: Oct. 3, 1997

(87) PCT Pub. No.: WO96/33232

PCT Pub. Date: Oct. 24, 1996

(30) Foreign Application Priority Data

Apr. 16, 1995 (DE) ............................................... 195 13 493
Apr. 30, 1995 (DE) ............................................... 195 15 244

(51) Int. Cl.$^7$ .................................................... C07C 67/02
(52) U.S. Cl. ........................................... 560/263; 560/264
(58) Field of Search ................................... 560/263, 264, 560/203

(56) References Cited

U.S. PATENT DOCUMENTS

| | | |
|---|---|---|
| 4,127,513 | 11/1978 | Bellis . |
| 4,189,566 | 2/1980 | Mueller et al. . |
| 4,243,799 | 1/1981 | Mueller et al. . |
| 5,210,283 | 5/1993 | Kahn et al. . |

FOREIGN PATENT DOCUMENTS

| | | |
|---|---|---|
| 2801578 | 7/1979 | (DE) . |
| 2916653 | 11/1980 | (DE) . |

OTHER PUBLICATIONS

Römpp Chemie Lexikon; by Prof. Dr. J. Falbe (Düsseldorf) and Prof. Dr. M. Regitz (Kaiserlautern); Bearbeitet von Zahlreichen Fachkollegen Zentralredaktion: Dr. E. Hillen–Maske; Georg Thieme Verlag Stuttgart · New York 1991©; pp. 2850–2851.

Römpp Chemie LExikon; by Prof. Dr. J. Falbe (Düsseldorf) and Prof. Dr. M. Regitz (Kaiserlautern); Bearbeitet von Zahlreichen Fachkollegen Zentralredaktion: Dr. E. Hillen–Maske; George Thieme Verlag Stuttgart· New York©; pp. 299 and 451 and English translation.

14. Füllstoffe, Hilfsmittel; Sonderdruck aus dem Jahrbuch FÜr Den Praktiker 1981 (Augsburg); Attapulgit—Eigenschaften un Anwendung; by D. Nobel; pp. 355–363 and English translation.

*Primary Examiner*—Paul J. Killos
(74) *Attorney, Agent, or Firm*—Fulbright & Jaworski, LLP

(57) ABSTRACT

An improved process for the preparation of polytetramethylene ether glycol diesters of the formula $$R\text{—CO—O}(\text{—CH}_2\text{-CH}_2\text{-CH}_2\text{-CH}_2\text{-O})_n\text{-COR}_1$$

in which R and $R_1$ are identical or different and are an alkyl radical or a derivative thereof, by polymerization of tetrahydrofuran in the presence of a fixed-bed polymerization catalyst and a carboxylic acid anhydride.

Through use of neutral or weakly basic magnesium-aluminium hydrosilicates instead of the known acidic montmorillonite, zeolite or kaolin catalysts, polymers with more uniform properties and a narrower molecular weight distribution are obtained at a higher rate of polymerization, even when technical-grade tetrahydrofuran is used.

16 Claims, No Drawings

PROCESS FOR PRODUCING POLYTETRAMETHYLENE ETHER GLYCOL DIESTER ON ALUMINIUM MAGNESIUM SILICATE CATALYSIS

BACKGROUND AND SUMMARY OF THE INVENTION

This invention relates to a process for the preparation of polytetramethylene ether glycol (PTMEG) diesters of the formula R—CO—O(—$CH_2$-$CH_2$-$CH_2$-$CH_2$-O)$_n$—$COR_1$, wherein R and $R_1$ are identical or different and are an alkyl radical or a derivative thereof, and n is preferably an integer from 2 to 200, by polymerization of tetrahydrofuran (THF) in the presence of carboxylic acid anhydride using a neutral or slightly basic magnesium-aluminium hydrosilicate catalyst that has been activated by heating to 200–600° C. The natural minerals sepiolite and, in particular, attapulgite, are suitable raw materials for the new catalysts of this invention.

The polymerization of THF by means of oxonium ion catalysis became known as a result of the basic research work carried out by H. Meerwein et. al. (Angew. Chemie 72, (1960), 927), and is treated comprehensively in the monograph "Polytetrahydrofuran" by P. Dreyfus, Gorden and Breach Sc. Publishers, New York, London, Paris 1982.

The German patent no. 2916653 describes a polymerization process for THF—that has been purified in a separate step—in which the polymerization takes place by means of bleaching earth in a fixed bed, in the presence of carboxylic acid anhydride. Bleaching earths are naturally occurring aluminium silicates with a cryptocrystalline three-layer structure of the montmorillonite mineral. The mineral, obtained from deposits thereof, exhibits physical and chemical properties which vary depending on the origin. This applies in particular to the activity of the catalysts, which is not constant but varies from batch to batch. Despite the low price, this poses a serious disadvantage with regard to the commercial use of bleaching earths as catalysts. Kaolin and zeolites, proposed in the PCT application no. WO 94/05719 for THF poymerizatation, have similar disadvantages. These minerals do not become active catalysts until they have undergone acid treatment. An added disadvantage of these minerals is that a commercially usable polymer is only obtained if the THF is extremely pure.

The object of the present invention was thus to simplify the industrial-scale polymerization of THF and to render it reproducible, at the same time retaining the advantages—particularly that of fixed-bed catalysis—of the method described in German patent no. 2916653.

Surprisingly, it was found that granular or pelletized sepiolite and attapulgite which are largely free from water and are either neutral-to-weakly-basic (pH=7–9.5) or else protonated as a result of acid treatment, when suspended, or, better, when introduced into a stationary, fixed catalyst bed, convert a mixture of THF and carboxylic acid anhydride reproducibly into the carboxylic ester of polytetrabutylene ether glycol at a high polymerization rate, the ester so formed having a low color index and the catalyst being active over an unusually long period of time. The THF does not need to be specially purified as in the case of bleaching earths, zeolites or kaolin, and even THF containing water (e.g. 1% water) can be polymerized. Through use of attapulgite, in particular, as catalyst, polymers are obtained which have a very low color index, a narrow molecular weight distribution and an extremely low content of crown ether imputities. Attapulgite is used with preference in the process according to the invention.

The catalyst remains active for a practically unlimited period of time, this being an added reason for the better environmental compatibility of the new process.

DETAILED DESCRIPTION OF THE INVENTION

Sepiolite and attapulgite are naturally widespread, hydrated magnesium-aluminium silicates, which catalyze THF polymerization without requiring special acid activation. Unlike the above-mentioned catalysts, these new catalysts are thus neutral or weakly basic, and since they contain no residual acid they are not corrosive. Their industrial use therefore has economic advantages, too. In the U.S. Pat. No. 5,210,283, the importance of subjecting bleaching earch catalysts to acid treatment is stressed and discussed in detail. It was not possible to develop the preferred embodiment of the process according to this invention, using neutral or weakly basic catalysts, without first overcoming this prejudice. Catalysts for the process of the invention include those known as Attapulgus Clay or the floridin earths. The preferred catalysts consist predominantly of the mineral attapulgite, made up of three-dimensional chains with the ideal chemical composition $(OH_2)_4(OH)_2Mg_5Si_8O_{20} \times 4 H_2O$.

In contrast to clays and kaolin, attapulgite and sepiolite contain magnesium, an element which is more strongly basic than aluminium; accordingly, one would expect these catalysts to be cationically less effective. Surprisingly, however, they are extremely active in the cationic polymerization of THF.

Water is removed from natural attapulgite by means of extrusion and controlled calcination. By grinding and screening, the catalyst is obtained in granular form or as a powder, which can be used in a suspension process or as a fixed-bed catalyst.

Prior to their use, the catalysts to be used according to the invention should be calcined, e.g. for a period of 0.5 to 10 hours, at a temperature in the range from 200 to 600° C. In this way the water content is reduced and the reactivity increased.

The granules used in the fixed-bed range in size from 2.4–4.75 mm=⅛ mesh. Attapulgite powder can also be stirred to a paste with water, pressed to pellets and calcined.

Instead of the naturally-occurring minerals, use can also be made of synthetic aluminium-magnesium hydrosilicates. These are obtainable from hydrolyzable mixtures of aluminium-magnesium-silicon compounds.

Only a small quantity of catalyst is required to polymerize THF. The dry catalyst is poured into a reactor, for example a tube or a shaft furnace. The dimensions of the catalyst bed are preferably selected according to the need to dissipate the heat of polymerization. It may also be useful to circulate all or some of the reaction product over the bed by pumping; in this way, by cooling or warming in a heat exchanger, isothermal reaction conditions can be ensured along the length of the furnace. In general, it is sufficient if the quantity of reaction product circulated hourly corresponds to about 3 to 10 times the reactor volume. During continuous polymerization, fresh feed in the form of THF and carboxylic anhydride is added to the circulating reaction product in an amount equivalent to 0.01–0.1 times the hourly circulating quantity thereof.

Another suitable type of reactor for polymerization reactions according to the invention is a rotating basket filled with granular catalyst; said basket is located in a reactor which can be controlled thermostatically and which may additionally be equipped with a stirring paddle.

Surprisingly, and a technical improvement on the procedure used hitherto and described, e.g., in German patent no. 29 16653, the products obtained using the process of the invention have a very narrow molecular weight distribution and a negligible quantity (less than 0.1 wt. %) of crown-ether impurities. While commercially available polytetramethylene ether glycol (PTMEG), with a molecular weight of 1000, is characterized by a polydispersity $M_w/M_n$ of 1.6 to 1.8, products obtained according to the invention have a polydispersity $M_w/M_n$ of 1.2 to 1.4. This is particularly suitable for the production of elastic polyurethane fibers or thermoplastic polyurethanes with excellent low temperature characteristics.

The essentially anhydrous attapulgite and sepiolite do not develop their catalytic activity until in the presence of the promotor carboxylic anhydride. It is of advantage to use only such carboxylic acid anhydrides as are derived from aliphatic or aromatic poly- and/or, preferably, monocarboxylic acids with 2 to 12 or preferably 2 to 8 carbon atoms. Examples of such anhydrides are acetic anhydride, propionic anhydride, butyric anhydride and also acrylic anhydride, methacrylic anhydride and succinic anhydride. Mixed anhydrides and mixtures of anhydrides may also be used. For reasons of cost, preference is given to acetic acid anhydride.

As already mentioned, the process of the invention can be used to prepare diesters of polybutylene glycol ether of any desired degree of polymerization. The concentration of carboxylic acid anhydride in the polymerization mixture determines the degree of polymerization. The lower the concentration of anhydride, the higher the molecular weights, and vice versa. The following guide values refer to a reaction temperature of 50° C.:

Degree of polymerization 8 9 10 24 Wt. % acetic anhydride in the polymerization recipe 10 8.5 6.8 3

Polymerization is effected by bringing fixed-bed catalysts into contact with the reaction mixture, for instance by pumping, in a suitable reactor; in the case of the preferred embodiment for example, where there is no gas phase, in a so-called "flooded, plug-flow reactor" (liquid-phase hydrogenation). The heat of reaction generated during polymerization is dissipated in a suitable manner. When carrying out the process of the invention in the simplest manner, it is also possible just to cover t he catalyst bed with reactio n mixture and have the reaction proceed adiabatically. With very active catalysts, boiling THF limits the maximum temperature to some 65° C. When the reaction is carried out in this way, polymerization is complete after about 30 to 60 minutes.

In general, polymerization is carried out at pressures between 0 and 25 bar and at temperatures between 10 and 60° C. There are no advantages in using lower or higher pressures and temperatures.

In most cases polymerization is allowed to proceed until all of the carboxylic anhydride has reacted. Depending on the polymerization temperature, 40 to 75 wt. % of the THF employed will have reacted if polymerization was carried out between 30 and 55° C. Unreacted THF can be recovered by distilling the reaction product and can be used again in further polymerization reactions to no disadvantage.

The polybutylene ether glycol diesters obtained with the process of the invention can be hydrolyzed using known methods, or else, using the method described in U.S. Pat. No. 2,499,725 for example, transesterified—for instance with methanol. Where the process is used on an industrial scale, hydrotransesterification as is described in the U.S. Pat. No. 4,608,422 is recommended. Other methods are described in German patent no. 2760272 and in European Patents 0185553 and 0038009. The simplest procedure is to transform the diesters into diols using Adkins' method of ester hydrogenation with copper/chromium oxide catalysts. There are suitable commercial catyalysts available. An example thereof are the copper chromite catalysts with 5–15% barium, which, at 220° C. and 250 bar hydrogen pressure, either without a solvent or alternatively in the presence of methanol or ethanol, transform the diesters without any losses into PTMEG. The latter, with molecular weights ranging, e.g., from 800–3000, is then suitable for the production of polyesters or polyurethanes. The products obtained according to the method of the invention can be hydrogenated using the Adkins method to products with a sufficiently low residual ester number of <1 mg KOH/g. PTMEG diacetates, which are obtained using other polymerization methods (e.g. by montmorillonite catalysis), result in polytetramethylene ether glycols that have residual ester numbers of more than 1 mg KOH/g.

The following examples serve to explain the process of the invention in more detail, without implying any limitations. Parts are parts by weight and bear the same relation to parts by volume as that of kilograms to liters.

DETAILED DESCRIPTION OF THE PREFERRED EMBODIMENTS

EXAMPLE 1

Attapulgus Clay/Floridin ⅛ mesh LVM (granular) from the company Chemie-Mineralien AG u. Co KG in Bremen was calcined for 2 hours at 300° C. and then cooled in a dessicator. 150 cm³ of the anhydrous granules were introduced into a Duran glass laboratory flask from the company Schott in Mainz, preheated to 50° C. in a water bath and covered with 300 g of a mixture comprising 91.5 wt. % technical-grade THF and 8.5 wt. % acetic anhydride. The flask, tightly sealed with a polypropylene screw cap, was rotated slowly about its longitudinal axis for 4 hours in the water bath at 50° C. in order to keep the catalyst bed in gentle motion.

The reaction mixture was then decanted off from the catalyst and analyzed. The acid number of the reaction product indicates that approximately 99% of the acetic anhydride had reacted.

In a film-type evaporator, the unreacted THF was evaporated off at 150° C. and 1 mbar from the formed polytetramethylene ether glycol diacetate, that made up 56 wt. % of the reaction solution. The saponification number of the diester was 152.6 mg KOH/g, which corresponds to a molecular weight of 734 g/mol. By means of transesterification with the same amount of methanol and in the presence of, for example, 0.01 wt. % sodium methoxide, PTMEG was obtained with a hydroxyl number of 173 mg KOH/g and a color index of 5 APHA. The product exhibits a very narrow molecular weight distribution. The heterogeneity quotient (polydispersity) $M_w/M_n$ is only 1.20. The proportion of oligomeric cyclic ethers is less than 0.01 wt. %.

EXAMPLE 2

The polymerization was carried out at 50° C. with the same experimental setup described for Example 1, using the commercially available, granular Attapulgus Clay ⅛ mesh LVM from the company Chemie MineralAG in Bremen. The catalyst was dried for 3 hours at 250° C. to constant weight. For the polymerization, use was made of a 3 wt. % solution of acetic anhydride in technical-grade THF. After 2.5 hours of polymerization the acetic anhydride had reacted to an extent of over 99%, and the polymer solution contained 53 wt. % PTMEG diacetate with an ester number of 61.2 (corresponds to a molecular weight of 1824 gmol). By means of liquid-phase hydrogenation on a fixed-bed barium-oxide-activated copper chromite catalyst at 220° C. and 250 bar hydrogen pressure, the diacetate, in 60 wt. % methanol solution, was converted into PTMEG with a hydroxyl number of 64.1 (molecular weight 1750 g/mol). The polymer, obtained by evaporating off the solvent (1 mbar, 190° C.), is very homogeneous, exhibiting a polydispersity $M_w/M_n = 1.5$ in the GPLC analysis. The color index is 5 APHA.

EXAMPLE 3

THF was polymerized as described in Example 1, but with other acid anhydrides. Instead of using 8.5 wt.% acetic anhydride, use was made of:
1. 16 wt. % butyric anhydride,
2. 24 wt. % 2-ethyl hexanoic anhydride or
3. 21 wt. % benzoic anhydride, producing polymer solutions of
1. 55 wt. % PTMEG dibutyrate,
2. 60 wt. % PTMEG di-2-ethyl hexonate
3. 58 wt. % PTMEG dibenzoate.

As described above, the esters were converted using various methods into PTMEG with the hydroxyl numbers
1. 168 mg KOH/g
2. 170 mg KOH/g and
3. 166 mg KOH/g.

EXAMPLE 4

Attapulgus Clay/Floridin 4/8 mesh LVM (granular) from the company Chemie-Mineralien AG u. Co KG in Bremen was covered with 0.2 wt. % hydrochloric acid and the excess solution sucked off with a Bujchner funnel. The granules were washed with distilled water prior to being calcined at 300° C. for 2 hours, and then cooled in a dessicator. 150 cm$^3$ of the dried granules were introduced into a Duran glass laboratory flask from the company Schott in Mainz, preheated to 50° C. in a water bath and covered with 300 g of a mixture comprising 91.5 wt. % technical-grade THF and 8.5 wt. % acetic anhydride. The flask, tightly sealed with a polypropylene screw cap, was rotated slowly about its longitudinal axis for 4 hours in the water bath at 50° C. in order to keep the catalyst bed in gentle motion.

The reaction mixture was then decanted off from the catalyst and analyzed. The acid number of the reaction product indicates that approximately 99% of the acetic anhydride had reacted.

The unreacted THF was evaporated off at 150° C. and 2 mbar from the polytetramethylene ether glycol diacetate, that made up 56 wt. % of the reaction solution. The saponification number of the diester was 154 mg KOH/g, which corresponds to a molecular weight of 730 gmol. Transesterification with the same amount of methanol in the presence of, for example, 0.01 wt. % sodium ethoxide produces PTMEG with a hydroxyl number of 173 mg KOH/g and a color index of 5 APHA. The product exhibits a very narrow molecular weight distribution. The heterogeneity quotient (polydispersity) $M_w/M_n$ is only 1.20. The proportion of oligomeric cyclic ethers is less than 0.01 wt. %.

Other embodiments of the invention will be apparent to those skilled in the art and are intended to be within the scope of the claims appended hereto.

What is claimed is:

1. A process for the preparation of polytetramethylene ether glycol diesters of the formula R—CO—O(—CH$_2$-CH$_2$-CH$_2$-CH$_2$-O)$_n$-COR$_1$ wherein R and R$_1$ are identical or different and are each an alkyl radical or a derivative thereof, and n is an integer from 2 to 200, comprising polymerizing tetrahydrofuran in the presence of a polymerization catalyst comprising a calcined magnesium-alminum hydrosilicate, wherein said magnesium-aluminum hydrosilicate is neutral, weakly basic or protonated and is a natural or synthetic attapulgite or sepiolite.

2. The process of claim 1, wherein said polymerization catalyst has a water content of less than 2%.

3. The process of claim 1, wherein said polymerization catalyst is selected from the group consisting of natural attapulgite and natural sepiolite.

4. The process of claim 2, wherein said polymerization catalyst is selected from the group consisting of natural attapulgite and natural sepiolite.

5. The process of claim 1, wherein said polymerization catalyst is disposed in a fixed bed and a mixture of said tetrahydrofuran and said carboxylic acid anhydride is passed over said fixed bed.

6. The process of claim 2, wherein said polymerization catalyst is disposed in a fixed bed and a mixture of said tetrahydrofuran and said carboxylic acid anhydride is passed over said fixed bed.

7. The process of claim 3, wherein said polymeriaton catalyst is disposed in a fixed bed and a mixture of said terydrofan and said carboxylic acid anhydride is passed over said fixed bed.

8. The process of claim 4, wherein said polymerization catalyst is disposed in a fixed bed and a mixture of said tetrahydrofuran and said carboxylic acid anhydride is passed over said fixed bed.

9. The process of claim 1, wherein said polymerization catalyst is thermally pretreated at a temperature of from 200° C. to 600° C. for 0.1 to 5 hours prior to use.

10. The process of claim 2, wherein said polymerization catalyst is thermally pretreated at a temperature of from 200° C. to 600° C. for 0.1 to 5 hours prior to use.

11. The process of claim 3, wherein said polymerization catalyst is thermally pretreated at a temperature of from 200° C. to 600° C. for 0.1 to 5 hours prior to use.

12. The process of claim 4, wherein said polymerization catalyst is thermally pretreated at a temperature of from 200° C. to 600° C. for 0.1 to 5 hours prior to use.

13. The process of claim 5, wherein said polymerization catalyst is thermally pretreated at a temperature of from 200° C. to 600° C. for 0.1 to 5 hours prior to use.

14. The process of claim 6, wherein said polymerization catalyst is thermally pretreated at a temperature of from 200° C. to 600° C. for 0.1 to 5 hours prior to use.

15. The process of claim 7, wherein said polymerization catalyst is thermally pretreated at a temperature of from 200° C. to 600° C. for 0.1 to 5 hours prior to use.

16. The process of claim 8, wherein said polymerization catalyst is thermally pretreated at a temperature of from 200° C. to 600° C. for 0.1 to 5 hours prior to use.

* * * * *